(12) United States Patent
Sui

(10) Patent No.: US 7,407,781 B2
(45) Date of Patent: Aug. 5, 2008

(54) OOCYTE RECORDING CHAMBER

(75) Inventor: Jinliang Sui, Northborough, MA (US)

(73) Assignee: Wyeth, Madison, NJ (US)

( * ) Notice: Subject to any disclaimer, the term of this patent is extended or adjusted under 35 U.S.C. 154(b) by 547 days.

(21) Appl. No.: 10/434,412

(22) Filed: May 8, 2003

(65) Prior Publication Data

US 2004/0000901 A1    Jan. 1, 2004

Related U.S. Application Data

(60) Provisional application No. 60/378,822, filed on May 8, 2002.

(51) Int. Cl.
| C12M 1/00 | (2006.01) |
| C12M 3/00 | (2006.01) |
| C12M 1/36 | (2006.01) |
| C12M 1/38 | (2006.01) |
| C12N 9/00 | (2006.01) |
| C12N 11/00 | (2006.01) |

(52) U.S. Cl. .............. 435/173.1; 435/285.1; 435/286.5; 435/286.7; 435/287.9; 435/288.5; 435/285.2; 435/470; 435/287.1; 435/173.4; 324/200; 436/180; 436/63; 204/400; 204/403.01; 205/777.5

(58) Field of Classification Search .............. 435/285.2, 435/470, 285.1, 286.7, 287.9, 288.5; 324/200; 422/939; 436/180, 63; 204/400, 403.01; 205/777.5
See application file for complete search history.

(56) References Cited

U.S. PATENT DOCUMENTS

| 4,230,983 | A | * | 10/1980 | Steere et al. ............... 324/71.1 |
| 4,530,907 | A |   | 7/1985 | Peterson et al. |
| 4,650,766 | A |   | 3/1987 | Harm et al. |
| 4,734,372 | A |   | 3/1988 | Rotman |
| 4,810,650 | A |   | 3/1989 | Kell et al. |
| 4,983,527 | A |   | 1/1991 | Capco et al. |
| 5,262,128 | A | * | 11/1993 | Leighton et al. ............ 422/100 |

(Continued)

FOREIGN PATENT DOCUMENTS

CA        1169341        6/1984

(Continued)

OTHER PUBLICATIONS

Madeja et al. "A concentration-clamp system allowing two-electrode voltage-clamp investigations in oocytes of Xenopus lacvis". J. Neuroscience Methods, vol. 38, pp. 267-269, 1991.

(Continued)

Primary Examiner—William H. Beisner
Assistant Examiner—Nathan A Bowers
(74) Attorney, Agent, or Firm—Joseph E. Zahner

(57) ABSTRACT

An oocyte recording chamber for electrophysiological measurements. The recording chamber includes a base and a cover attached to the base. The cover and the base define a chamber having a size sufficient to accommodate an oocyte. The recording chamber includes a first electrode and a second electrode that are positioned so that the tips of the electrodes penetrate the membrane of the oocyte when the cover is fastened to the base. The recording chamber also includes a third electrode and a fourth electrode exposed to the chamber and used as ground electrodes.

11 Claims, 15 Drawing Sheets

U.S. PATENT DOCUMENTS

| | | | |
|---|---|---|---|
| 5,312,731 A | 5/1994 | Engström | |
| 5,424,209 A | 6/1995 | Kearney | |
| 5,432,086 A | 7/1995 | Fränzl et al. | |
| 5,449,492 A | 9/1995 | Krishtal | |
| 5,496,697 A | 3/1996 | Parce et al. | |
| 5,612,188 A | 3/1997 | Shuler et al. | |
| 5,621,007 A | 4/1997 | Gribkoff et al. | |
| 6,032,062 A * | 2/2000 | Nisch | 600/372 |
| 6,048,722 A | 4/2000 | Farb et al. | |
| 6,048,772 A | 4/2000 | D'Anna | |
| 6,268,168 B1 | 7/2001 | Farb et al. | |
| 6,277,559 B2 | 8/2001 | Takeshita et al. | |
| 6,329,154 B2 | 12/2001 | Takeshita et al. | |
| 6,329,194 B2 | 12/2001 | Takeshita et al. | |
| 6,338,960 B2 | 1/2002 | Takeshita et al. | |
| 6,541,243 B1 * | 4/2003 | Harris et al. | 435/285.1 |
| 6,695,765 B1 * | 2/2004 | Beebe et al. | 600/33 |
| 6,699,697 B2 * | 3/2004 | Klemic et al. | 435/173.4 |
| 6,773,669 B1 * | 8/2004 | Holaday et al. | 422/44 |
| 2001/0011154 A1 * | 8/2001 | Kato et al. | 600/345 |
| 2003/0070923 A1 * | 4/2003 | Schroeder et al. | 204/400 |
| 2004/0115679 A1 * | 6/2004 | Tanioka et al. | 435/6 |

FOREIGN PATENT DOCUMENTS

| | | |
|---|---|---|
| DE | 2431198 | 1/1976 |
| EP | 0336974 | 9/1998 |
| SU | 1346672 | 10/1987 |

OTHER PUBLICATIONS

Derwent Abstract, AN 1982-05362E of Physiology Inst. SU 819169 (Apr. 7, 1981).0.

* cited by examiner

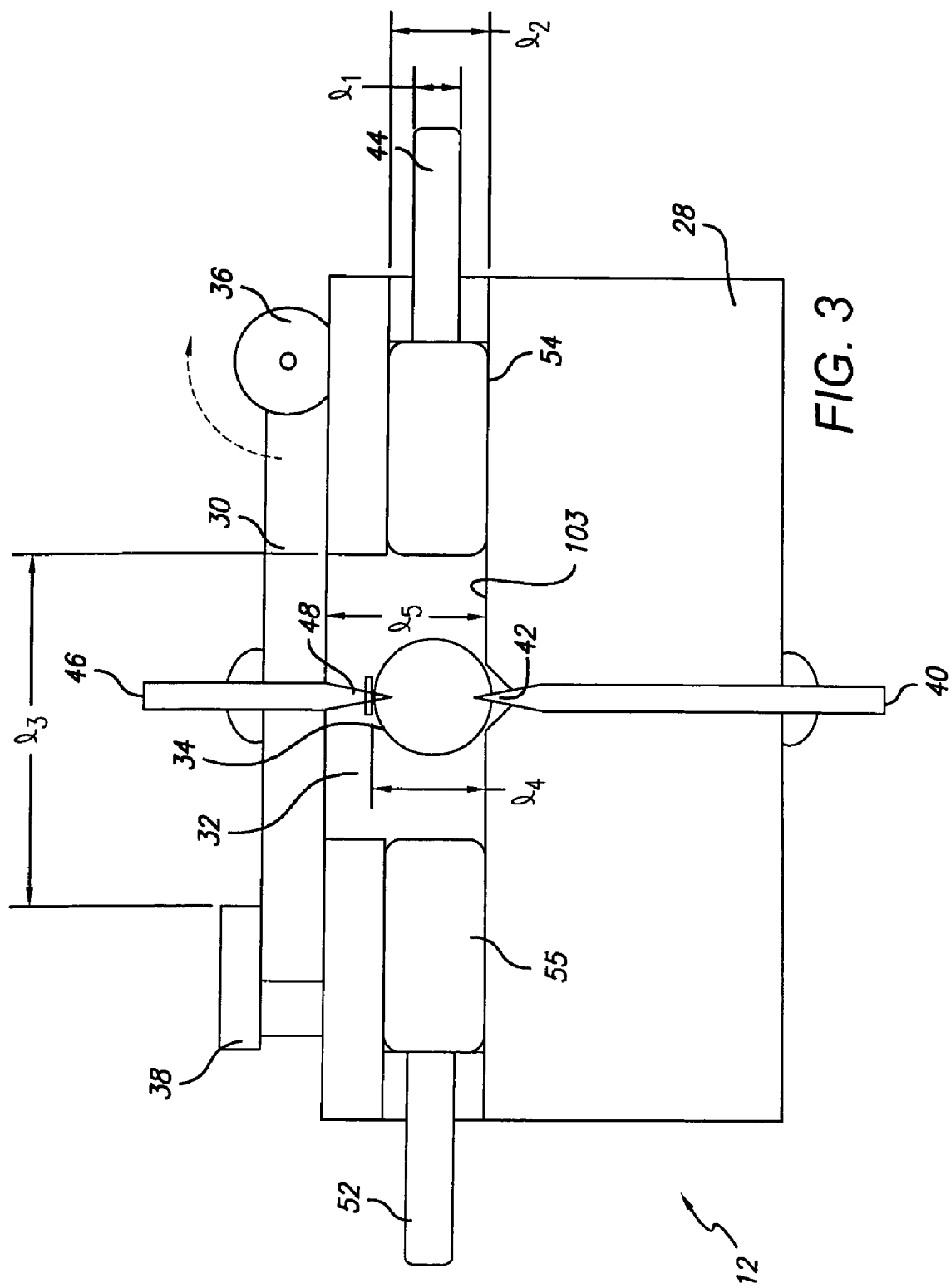

OOCYTE RECORDING CHAMBER

RELATED APPLICATIONS

The application claims priority to U.S. Provisional Patent Application Ser. No. 60/378,822, filed on May 8, 2002, entitled "OOCYTE RECORDING CHAMBER."

TECHNICAL FIELD

This invention relates to oocyte recording chamber.

BACKGROUND

Most cell membranes communicate with extracellular environment by means of receptor and channel proteins located within the cell membrane. Receptor and ion channel proteins can be gated by molecules which bind to the receptor and signal the binding event by opening the ion channels through which ions such as sodium and chloride ions can flow. Ion channels can also be gated by the cross membrane potentials through the voltage sensor components in the protein molecules. Like modulators of receptors, the levels of cross membrane potential can regulate such voltage-gated ion channel activities, generating most of the neuronal and muscular activities. Ionic flux across a cell membrane generates electrical current that can be measured with appropriate recording equipment. Such electrophysiological studies of receptor and ion channel function often utilize unfertilized eggs, or oocytes, taken from the South African clawed frog, Xenopus laevis. Xenopus oocytes have the ability to synthesize functional proteins when microinjected with exogenous mRNA or cDNA constructs.

In electrophysiological analysis, an oocyte is electrically connected to intracellular voltage and current measuring and clamping devices. FIG. 1A shows a side view of a prior art recording chamber 2 that accommodates an oocyte 3 immersed in a solution 4. A voltage electrode 9 and a current electrode 9 are held by manipulators 6 and positioned so as to contact the oocyte to measure intracellular voltage and current signals. Two ground electrodes 7 and 11 are coupled to the solution in the recording chamber by agar bridges 8. The oocyte's response to the solution may be measured by maintaining a constant voltage between voltage electrode 6 and ground electrode 7, and measuring the current changes flowing through current electrode 9 and ground electrode 11. FIG. 1B shows a top view of recording chamber 2, which is connected to a multi-barrel manifold 124 through an inlet 120. Manifold 124 allows different solutions to be diffused to recording chamber 2. An outlet 122 connected to a suction pump (not shown) allows solution 4 to flow out of recording chamber 2.

SUMMARY

In general, in one aspect, the invention is directed towards an apparatus that includes a base, a cover attached to the base, a first electrode having a tip, a second electrode having a tip, a third electrode, and a fourth electrode. The cover and the base define a chamber having a size sufficient to accommodate an oocyte having a membrane. The first and second electrodes are positioned so that the tips of the electrodes penetrate the membrane of the oocyte when the cover is fastened to the base. The third and fourth electrodes each have portions that are exposed to the chamber.

Implementations of the invention may include one or more of the following features. The cover is pivotly coupled to the base through a hinge, and movable between an open position to allow an oocyte to be placed in the chamber and a closed position to form a seal between the cover and the base. A rubber ring is placed between the cover and the base to provide a water-tight seal between the cover and the base when the cover is moved to the closed position.

The first and second electrodes protrude from the base and extend into the chamber. The first and second electrodes include a metal that is stable, highly conductive, and non-corrosive, such as platinum, silver, or a combination thereof. The surface of the first electrode exposed to the chamber are coated with silver/silver-chloride. The surface of the second electrode exposed to the chamber is coated with gold. The third and fourth electrodes are both embedded in the base with portions of the electrodes exposed to the chamber. The third electrode includes gold plated brass with a silver/silver-chloride pellet at one end of the third electrode that is exposed to the chamber.

A stopper, including non-conducting materials (such as plastic or epoxy-glass), is connected to the cover and configured to slightly press the oocyte towards the base, securing the oocyte position in the chamber when the cover is fastened to the base.

A portion of the base defines an indentation to receive the oocyte and to reduce movement of the oocyte in the chamber.

An isolation layer, such as non-conducting polyamide, is deposited on a portion of each of the first and second electrodes exposed to the chamber except for a small portion near a tip of each of the first and second electrodes. The portion near the tip that is not covered by the isolation layer may have a length between 50 to 100 microns. The portions of the electrodes exposed to the chamber may have lengths between 150 to 300 microns.

The second electrode may also protrude from the cover and extend into the chamber, with a stopper attached to the second electrode at a position between the cover and a tip of the second electrode, the stopper configured to slightly urge the oocyte towards the base when the cover is fastened to the base. A channel is provided to allow a fluid to flow into the chamber. Another channel is provided to allow the fluid to exit the chamber. A perfusion system is provided to perfuse the chamber with perfusion solutions each containing a different agent or concentration of an agent. A voltage clamp provides a voltage potential between the first and third electrodes. An ampere meter measures an amplitude of a current flowing through the second and fourth electrodes.

In general, in another aspect, the invention is directed towards an apparatus that includes a recording module, a perfusion system, a biosensor, and a computer. The recording module has a base and a cover attached to the base, the cover and the base defining a chamber having a size sufficient to accommodate a cell. The perfusion system perfuses the chamber with perfusion solutions. The biosensor is used to detect a response from the cell, and is coupled to the base and positioned to penetrate a membrane of the oocyte when the cover is fastened to the base. The computer collects, analyzes and displays responses detected by the biosensor.

In general, in another aspect, the invention is directed towards a method of assaying drug candidates that includes using an apparatus that includes a base, a cover attached to the base, a first electrode having a tip, a second electrode having a tip, a third electrode, and a fourth electrode. The cover and the base define a chamber having a size sufficient to accommodate an oocyte having a membrane. The first and second electrodes are positioned so that the tips of the electrodes penetrate the membrane of the oocyte when the cover is fastened to the base. The third and fourth electrodes each have portions that are exposed to the chamber.

In general, in another aspect, the invention is directed towards a method of measuring the biological effect of a candidate molecule. The method includes providing a recording module having a base and a cover attached to the base, the cover and the base defining a chamber having a size sufficient to accommodate a cell; providing a biosensor coupled to the base and facing the chamber; introducing the cell into the recording module; moving the cover to a closed position so that a water-tight seal is formed between the cover and the base; perfusing the chamber with perfusion solutions; and detecting a response of the cell to the solutions.

Implementations of the invention may include one or more of the following features. Moving the cover to the closed position simultaneously moves the cell towards the biosensor so that the biosensor penetrates a membrane of the cell. The perfusion solutions each comprise a candidate molecule.

In general, in another aspect, the invention is directed towards a method of identifying a drug, inhibitor, agonist, or antagonist. The method includes introducing a candidate or test compound (e.g., organic molecule, polypeptide) to an oocyte expressing a protein or target of interest, including ion channel proteins (e.g., sodium, calcium, chloride channels) in a recording chamber through a first channel. The recording chamber includes a base, a cover attached to the base, a first electrode having a tip, a second electrode having a tip, a third electrode, and a fourth electrode. The cover and the base define a chamber having a size sufficient to accommodate an oocyte having a membrane. The first and second electrodes are positioned so that the tips of the electrodes penetrate the membrane of the oocyte when the cover is fastened to the base. The third and fourth electrodes each have portions that are exposed to the chamber. The method further includes applying an electric potential between the first and third electrodes, and measuring a response from the oocyte using the second and fourth electrodes.

Implementations of the invention may include one or more of the following features. The response is used to determine whether the compound inhibits (or binds) or is an agonist or antagonist of the protein expressed in the oocyte.

In general, in another aspect, the invention is directed towards an apparatus that includes a base and a cover configured so that when the cover is secured to the base, the base and the cover in combination define a chamber having a size sufficient to receive an oocyte, the base defining an inlet and an outlet to allow a fluid to flow into and out of, respectively, the chamber. The apparatus also includes a first pair of electrodes positioned to contact the oocyte, and a second pair of electrodes positioned to be exposed in the chamber and spaced away from the oocyte.

Implementations of the invention may include one or more of the following features. The apparatus also includes gears to adjust positions of the first pair of electrodes. The first pair of electrodes comprise glass micropipettes. The apparatus also includes side covers to clamp the first pair of electrodes to the base at predetermined positions, the side covers clamping the first pair of electrodes with forces configured to allow the positions of the first pair of electrodes to remain adjustable.

In general, in another aspect, the invention is directed towards a method that includes placing an oocyte in a chamber defined by a base and a cover, the base including a first electrode and a second electrode protruding into the chamber, the oocyte positioned near the tips of the first and second electrodes; and closing the cover to urge the oocyte towards the tips of the first and second electrodes.

Implementations of the invention may include one or more of the following features. The method also includes penetrating a membrane of the oocyte using the tips of the first and second electrodes. The method also includes allowing a solution to flow into the chamber. The method also includes providing a predetermined voltage between the first electrode and a third electrode, the third electrode contacting the solution in the chamber and spaced apart from the first and second electrodes. The method also includes measuring a current flowing through the second electrode and fourth electrode, the fourth electrode contacting the solution in the chamber and spaced apart from the first, second, and third electrodes.

In general, in another aspect, the invention is directed towards a method that includes placing an oocyte in a chamber defined by a base and a cover; and inserting an electrode through a passage defined by the base so that a tip of the first electrode is positioned near the oocyte.

Implementations of the invention may include one or more of the following features. The method also includes using a side cover in combination with a base to hold the electrode. The method also includes adjusting the position of the electrode so that the tip of the electrode penetrate a membrane of the oocyte. Adjusting the position of the first electrode includes moving the electrode along a predefined axis towards the oocyte.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 shows a side view of an oocyte recording chamber.

Like reference symbols in the various drawings indicate like elements.

DETAILED DESCRIPTION

Figure 1A:
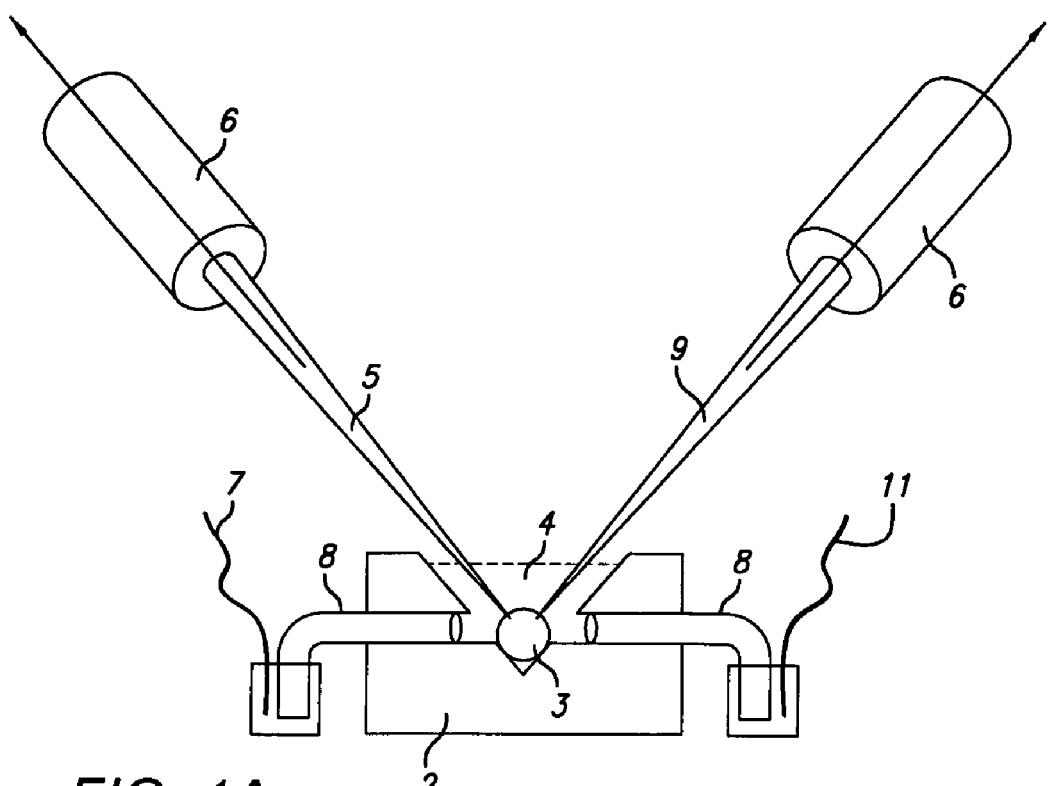
FIGS. 1A and 1B show an example of an oocyte recording chamber.
Figure 2:
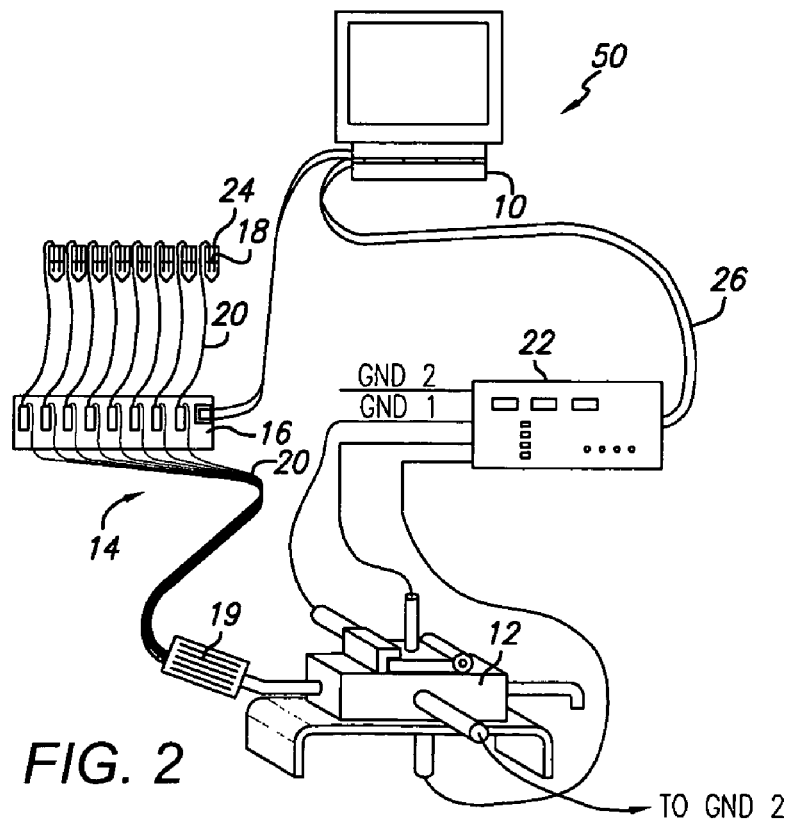
FIG. 2 shows an automated oocyte perfusion control system.
Figure 1B:
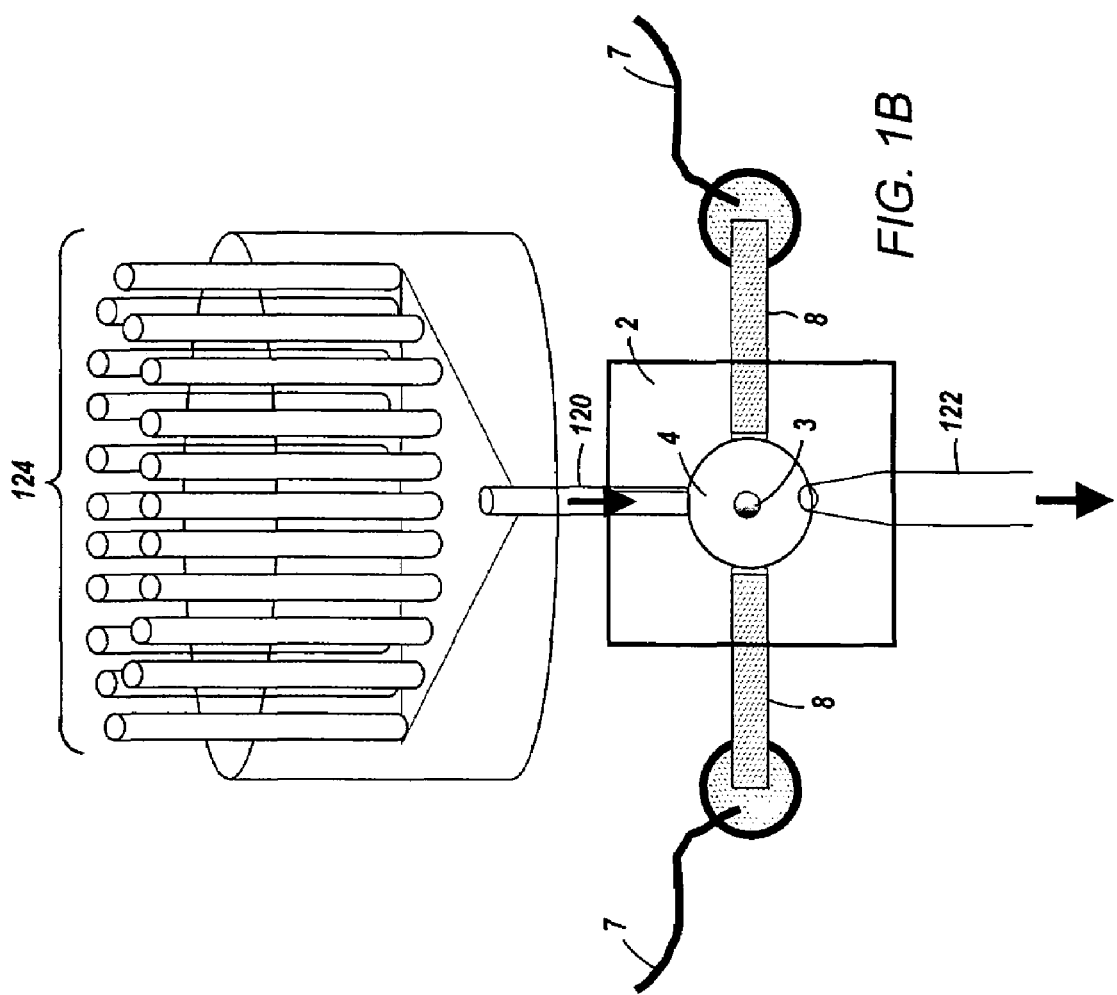

Referring to FIG. 2, an automated perfusion control system 50 includes a recording chamber 12 that receives an oocyte, a perfusion control system 14 for perfusing different solutions over the oocyte, and a computer 10 that controls the perfusion system and collects measurement data representing the oocyte's responses to the solutions. Solutions flow from reservoirs 18 to a multi-barrel manifold 19 through tubes 20. The flow of solutions is regulated by valve controllers 16 that are controlled by computer 10. Each reservoir 18 includes ventilation means 24 that allows gravity flow of the solution from the reservoir 18 through tube 20 when valve controller 16 is open. System 50 includes a data acquisition module 22 connected to computer 10 for acquiring and digitizing response signals from the oocyte. Digitized data is sent to the computer for further analysis.

Referring to FIG. 3, a side view of an example of a recording chamber 12 is shown. Recording chamber 12 includes a base 28 and a cover 30 that defines an oocyte chamber 32 that accommodates an oocyte 34. Cover 30 is rotatably coupled to base 28 through a hinge 36. A cover lock 38 secures cover 30 at a closed position to prevent movement of the cover during oocyte electrophysiological measurement. A current electrode 40 is embedded in base 28, and a tip 42 of electrode 40 protrudes from base 28 and extends into oocyte chamber 32. A ground electrode connector 44 (e.g., made of gold-plated brass) is embedded in the base 28 and connected to a pellet 54 (e.g., made of gold-plated brass) that is exposed to the oocyte chamber 32. A voltage electrode 46 is embedded in cover 30, and a tip 48 of electrode 46 protrudes from cover 30 and extends into oocyte chamber 32. A second ground electrode connector 52 (e.g., made of gold-plated brass) is embedded in base 28 and connected to a silver/silver-chloride (i.e., Ag—AgCl) pellet 55 that is exposed to the oocyte chamber 32.

Base 28 and cover 30 may be made of plastic, epoxy glass, or other materials that are stable, non-conductive to electric current, and do not react with perfusion solutions. The voltage electrode 46 and current electrode 40 may be made of stable, highly conductive, and non-corrosive material, such as silver or platinum. The voltage electrode may be coated with a material (such as silver/silver-chloride) to reduce junction potential when the electrode is put into the solution. A rubber seal (not shown in the figure), or O-ring, may be provided between cover 30 and base 28 so as to provide a water-tight seal between the cover and the base when the cover is closed.

In one example of recording chamber 12, the diameter $l_1$ of ground electrode connectors 44 is about 0.5 mm, the diameter $l_2$ of pellets 55 and 54 is about 1 mm, and the width $l_3$ of oocyte chamber 32 is about 3 mm. The vertical distance $l_4$ between plug 62 and a bottom surface 103 of oocyte chamber 32 is about 2 mm.

When electrophysiological measurements are conducted with the oocyte expressing a protein of interest, a solution containing an agent (e.g., GABA) fills the oocyte chamber 32 and covers oocyte 34. In one example, voltage electrode 46, current electrode 40, and ground electrode connectors 44 and 52 are connected to data acquisition module 22. Module 22 maintains a constant voltage difference between voltage electrode 46 and ground electrode connector 52 (e.g., 60 mV). Module 22 injects electric current from electrode 40 into the oocyte 34, and ground electrode connector 44 provides a return path for the current. The amount of current flowing through current electrode 40 and ground electrode connector 44 is measured at regular intervals. These current measurements represent the oocyte's response to the agent in the solution. By constructing a recording chamber 12 having a closed oocyte chamber 32 defined by base 28 and cover 30, the oocyte 34 and electrodes 40, 46 can be accurately positioned in a short amount of time.

Figure 4:
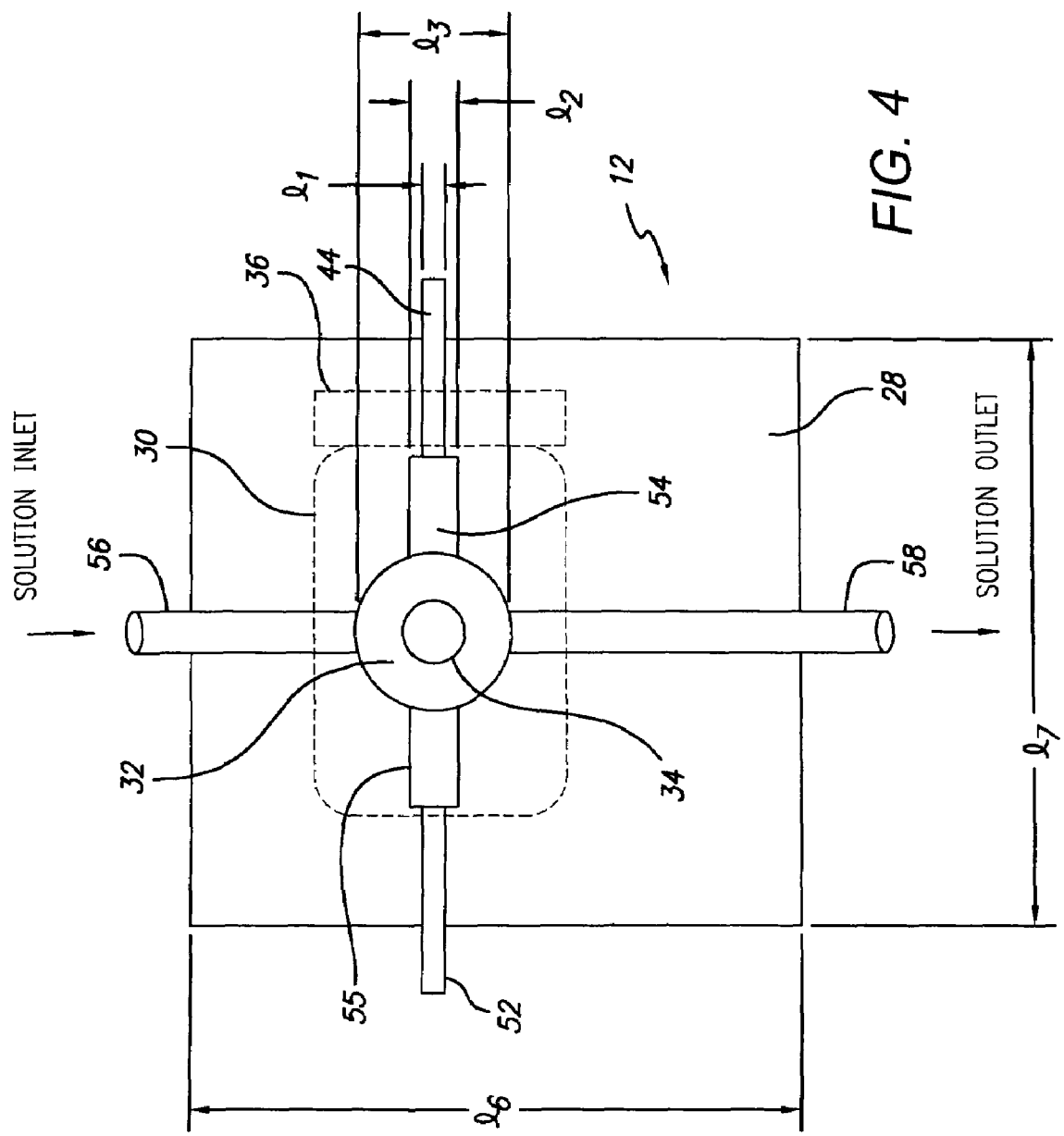
FIG. 4 shows a top view of an oocyte recording chamber.

Referring to FIG. 4 (where a top view of recording chamber 12 is shown), an inlet 56 allows a solution to enter oocyte chamber 32 and perfuse oocyte 34. An outlet 58 allows the solution to exit oocyte chamber 32. In one example, inlet 56 is connected to manifold 19, and the solution flows from reservoir 18 through tube 20, manifold 19, inlet 56, oocyte chamber 32, and outlet 58 due to gravitational force. No suction pump is used at outlet 58 to remove the solution from oocyte chamber 32.

Once the oocyte chamber 32 is filled with the solution, oocyte chamber 32 remains filled as long as there is sufficient solution in reservoir 18 and the valve controller 16 is kept open. This eliminates the time required to adjust the position of a suction tube when suction pumps are used to remove the fluid. This also eliminates solution level fluctuation problems that occur when suction pumps are used. Because fluctuation of solution level is eliminated, the oocyte may remain effective longer, and the oocyte response signals may be measured more accurately.

In an example of recording chamber 12, the diameter of inlet 56 is about 1 mm, and the diameter of outlet 58 is also about 1 mm. The base 28 of recording chamber 12 has a length $l_6$ of about 15 mm and a width $l_7$ of about 15 mm.

Figure 13:
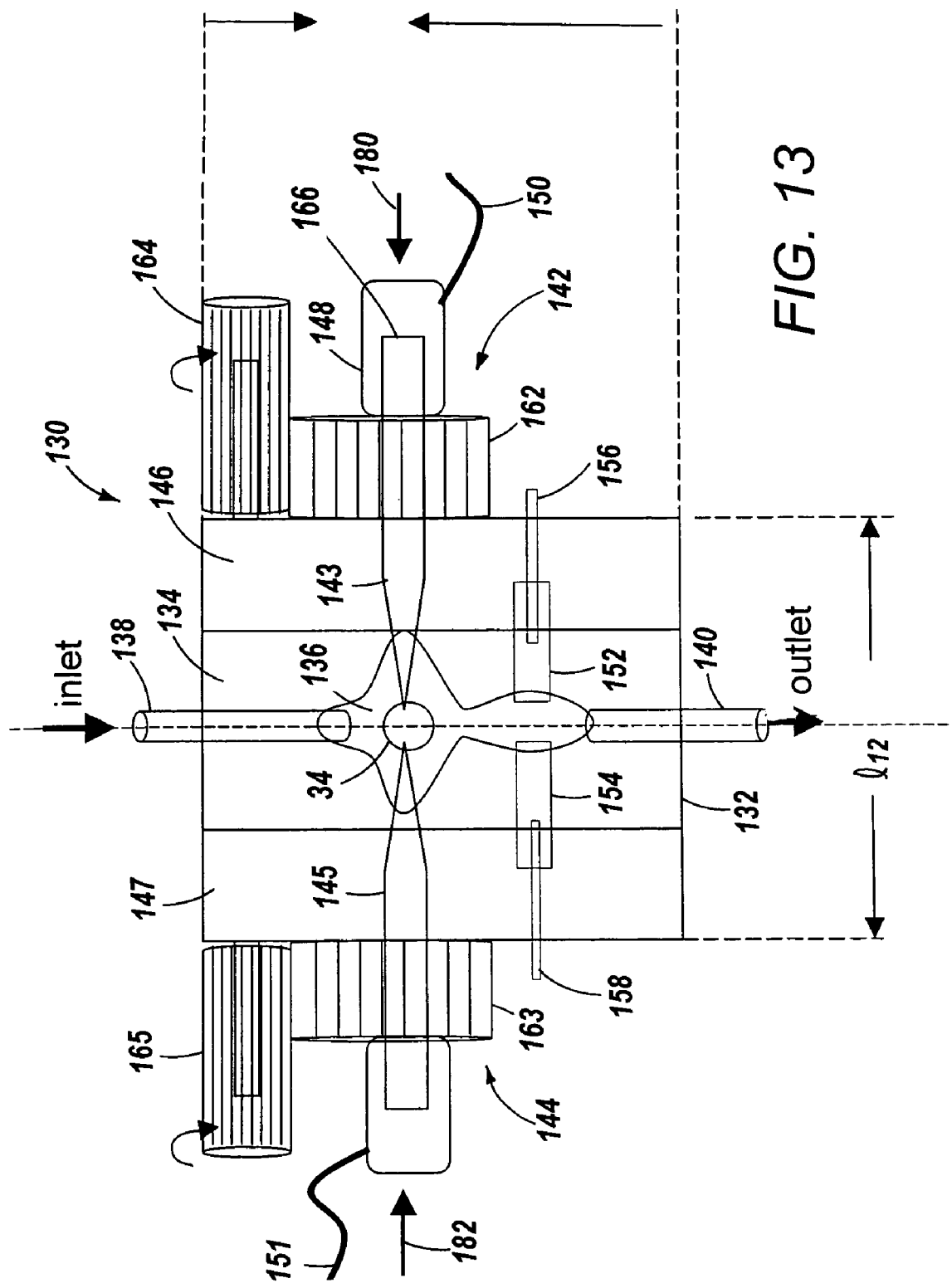
FIGS. 13 and 14 show a top view and a side view of an example of a recording chamber.
Figure 14:
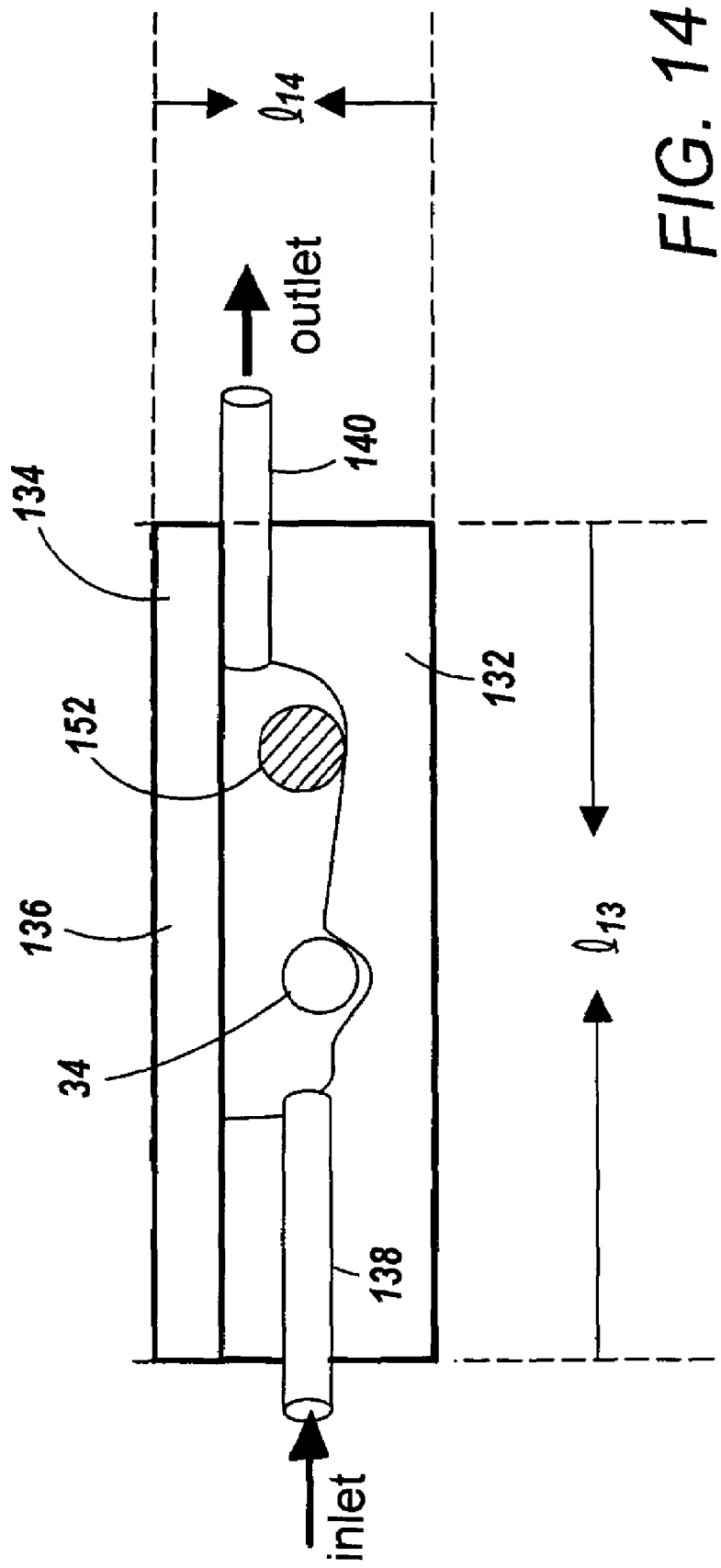

FIGS. 13 and 14 show a top view and a side view, respectively, of an example of a recording chamber 130. A base 132 and a center cover 134 defines an oocyte chamber 136 that accommodates an oocyte 34. Oocyte chamber 136 is connected to an inlet 138 and an outlet 140 to allow a solution to flow into oocyte chamber 136 and perfuse oocyte 34. A voltage electrode 142 includes a glass micropipette 143 filled with 3M KCl electrolyte solution. Micropipette 143 has an outer diameter of 1.5 mm, and an opening of 1 micron at its tip, which penetrates oocyte 34 during measurement of oocyte properties. Glass micropipette 143 is connected to an electrode connector cap 148 that contains 3M KCl solution. An electrode connector 150 connects the 3M KCl solution via the connector cap 148 to a reference voltage. Current electrode 144 has a configuration similar to voltage electrode 142, and includes a glass micropipette 145 filled with a 3M KCl electrolyte solution. Glass micropipette 145 has an outer diameter of 1.5 mm, and an opening of 1 micron at its tip, which penetrates oocyte 34 during operation.

Glass micropipettes 143 and 145 are inserted horizontally into oocyte chamber 136 through cavities formed between base 132 and side covers 146 and 147.

Figure 11:
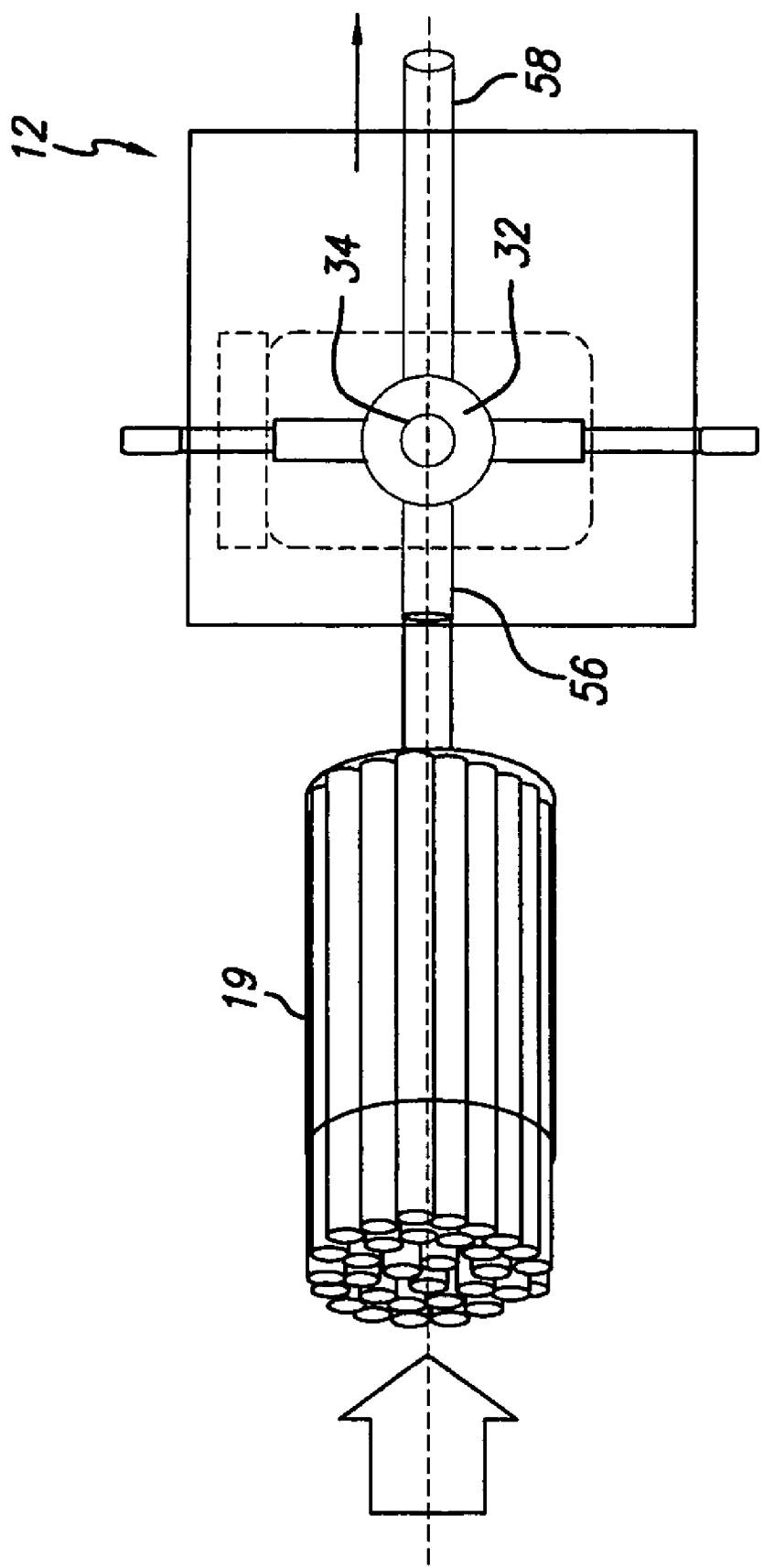
FIG. 11 shows a top view of an oocyte recording chamber with perfusion solutions.
Figure 12:
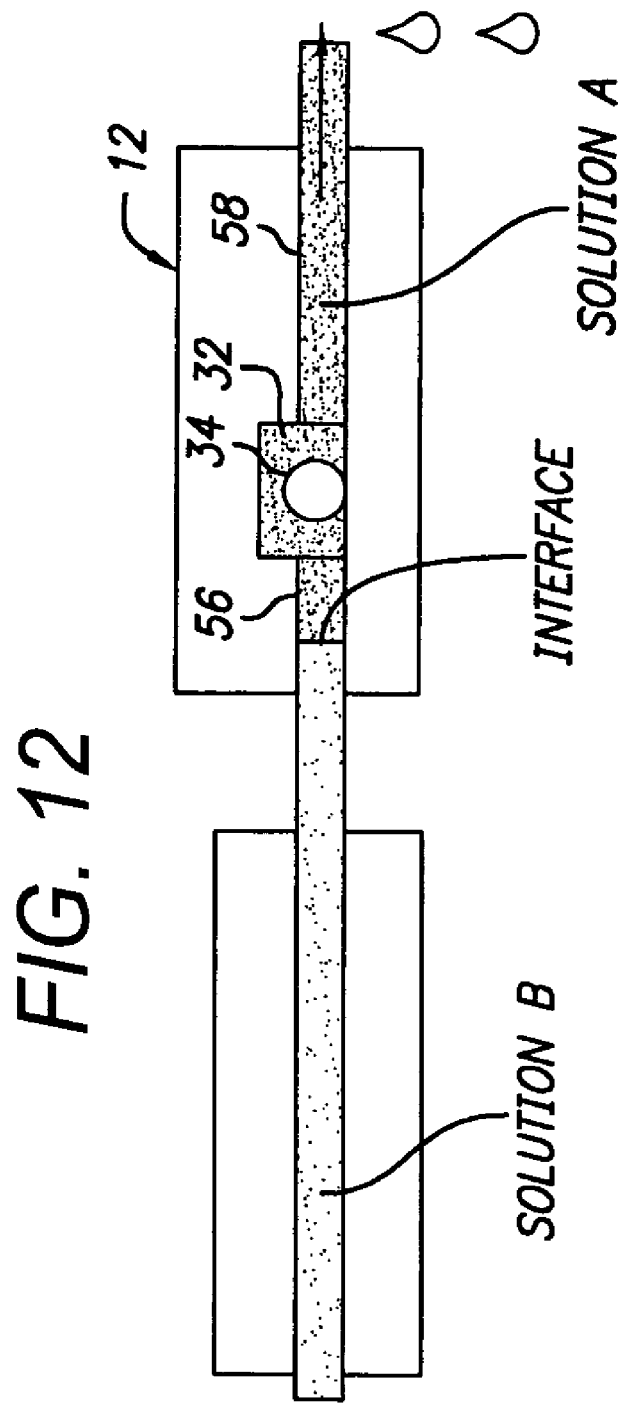
FIG. 12 shows a side view of the recording chamber of FIG. 1.

An advantage of using recording chamber 12 is that it allows precise control of the interface between different solutions that are perfused through the recording chamber. Referring to FIG. 11 (which shows a top view of recording chamber 12) and FIG. 12 (which shows a side view of the recording chamber), when a first solution A and a second solution B are perfused through oocyte 34, the solutions flow under the influence of gravity. Through gravitational force, solution B pushes the last portion of solution A through inlet 56, oocyte chamber 32, and outlet 58. A more clearly defined interface exists between solutions A and B when they flow under gravity than when they are removed from the oocyte chamber by a suction pump.

Figure 5:
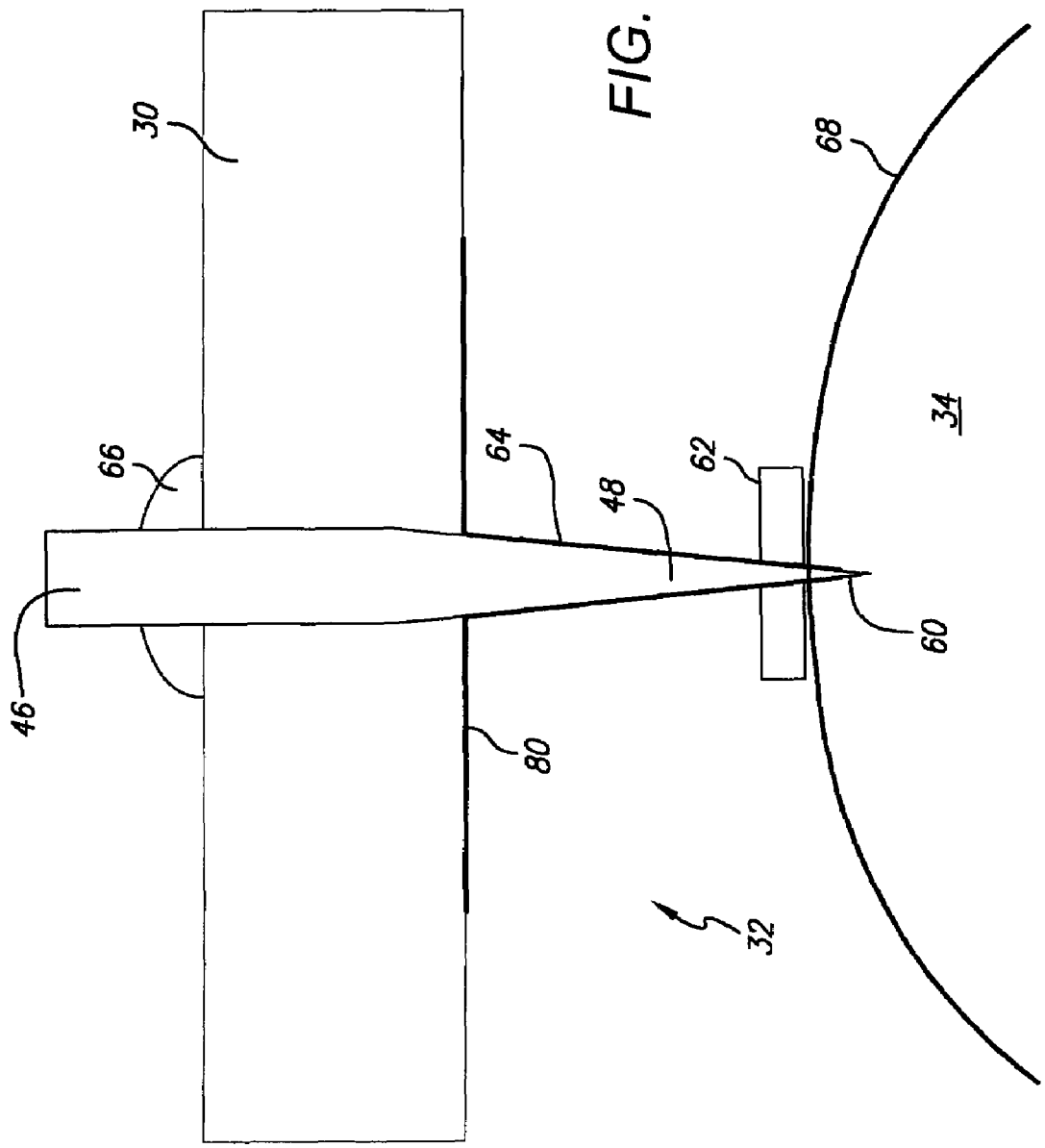
FIG. 5 shows a detailed view of a portion of the cover and an electrode.

Referring to FIG. 5, a more detailed view of the cover 30 and voltage electrode 46 is shown. Voltage electrode 46 is embedded in cover 30 and secured by a reinforcement material 66 (e.g., glue or resin). Voltage electrode 46 may be made of silver or platinum, and coated with silver/silver-chloride. Additionally, voltage electrode 46 is coated with a polyamide layer 64 for the portion of the electrode extending into oocyte chamber 32 except for a small portion at the tip 60 that penetrates a membrane 68 of oocyte 34 when cover 30 is closed. The polyamide layer 64 is an insulator that isolates tip 60 from the solution in oocyte chamber 32 so that a preset voltage difference may be maintained across the membrane 68 (i.e., a voltage difference is maintained between the oocyte within membrane 68 and the solution outside of membrane 68). In practice, when the polyamide layer 64 is coated on the voltage electrode 46, a portion of cover 30 near the voltage electrode will also be coated with polyamide. This will not affect the operation of the voltage electrode.

A stopper 62 is provided near the tip 60, and positioned so that when cover 30 is closed, stopper 62 may gently urge the oocyte downward towards base 28 so that the current electrode 40 may penetrate membrane 68, as described below. Stopper 62 may be made of the same material as the base and cover, such as plastic or epoxy glass.

Figure 6:
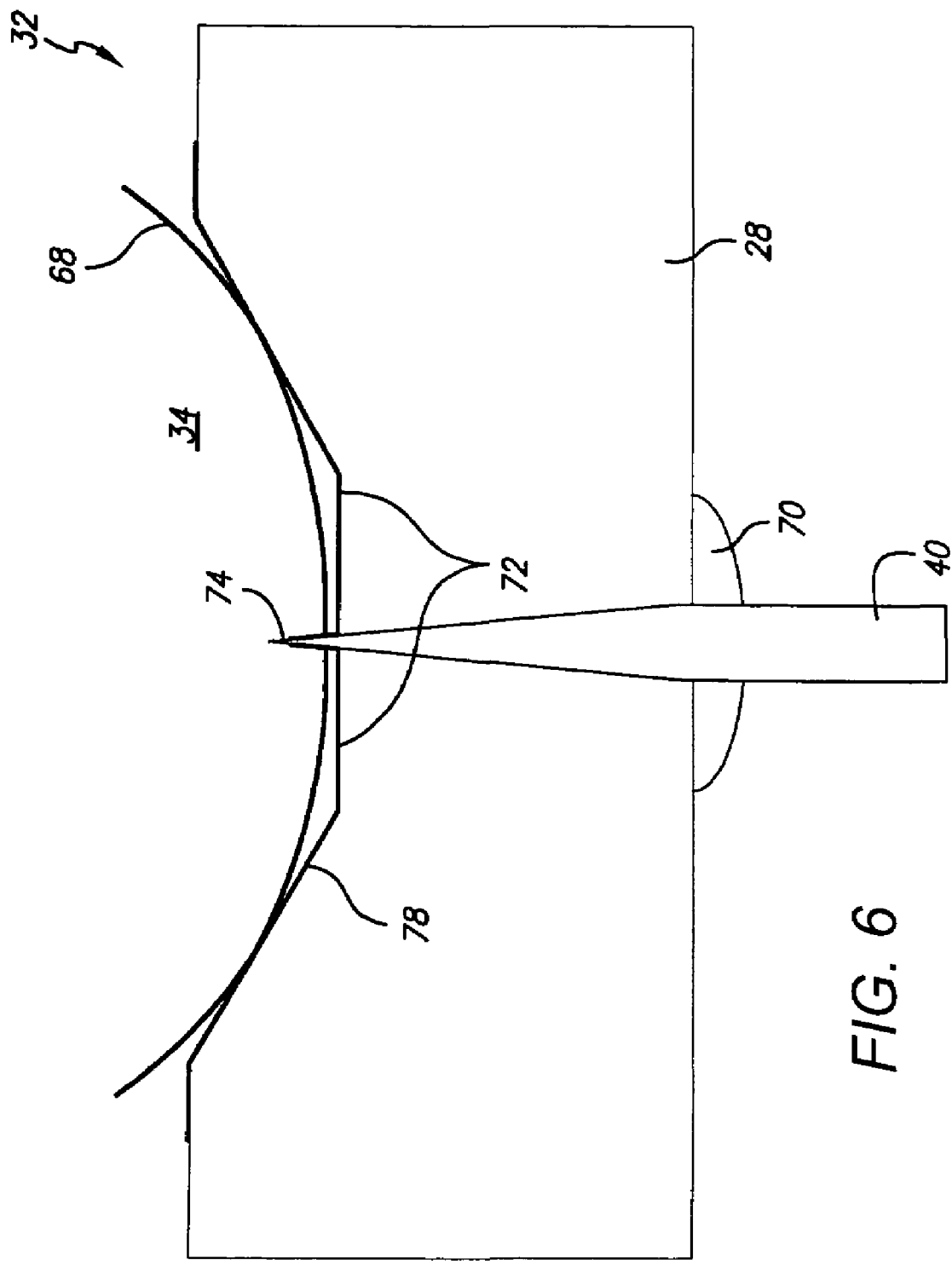
FIG. 6 shows a detailed view of a portion of the base and an electrode.

Referring to FIG. 6, a more detailed view of the base 28 and current electrode 40 is shown. Current electrode 40 is embedded in base 28 and secured by a reinforcement material 70 (e.g., glue or resin). Current electrode 40 may be made of silver or platinum. In one example, unlike voltage electrode 46, current electrode 40 is not coated with silver/silver-chloride. Current electrode 40 is coated with a polyamide layer 72 for the portion of the electrode extending into oocyte chamber 32, except for a small portion at the tip 74 that penetrates membrane 68 of oocyte 34 when cover 30 is closed. Polyamide layer 72 isolates tip 74 from the solution in oocyte chamber 32 so as to ensure that current injected into oocyte 34 will flow through membrane 68 before returning to ground electrode connector 44.

When an ion channel changes between a closed state and an opened state, the conductance of the membrane changes. When the voltage difference across membrane 68 is clamped, the ionic current flowing through membrane 68 will change in response to the changes in membrane conductance. By monitoring the current flowing through current electrode 40 and ground electrode connector 44, the ion channel activity changes in membrane 68 may be detected.

Base 28 includes an indent 78 that supports oocyte 34 at a relatively fixed position. Referring as well to FIG. 5, the distance between the center of indent 78 and a surface 80 of cover 30 is slightly larger than a diameter of the oocyte. Voltage electrode 46 and current electrode 40 are positioned so that when cover 30 is closed, the distance between tip 60 of electrode 46 and tip 74 of electrode 40 is smaller than the diameter of the oocyte. The polyamide layers 80 and 72 cover the electrodes 46 and 40, respectively, so that the tips 60 and 74 (without polyamide layers) are immersed entirely within the oocyte when the cover is closed. Stopper 62 is positioned so that when cover 30 is closed, stopper 62 slightly urges oocyte 34 against indent 78 and tip 74, so that tip 74 may penetrate membrane 68 when cover 30 is fully closed.

An advantage of using recording chamber 12 is that because the size of a Xenopus oocyte is relatively constant, the tips 60 and 74 will almost always penetrate the membrane of the oocyte when the cover 30 is closed. This eliminates the need to adjust the position of the electrodes 46 and 40 every time a new oocyte is placed into the recording chamber 12. This eliminates the cost of electrode manipulators used to adjust the electrodes, and the cost of microscopes or video cameras used to observe the precise positions of the electrode tips. Another advantage is that the oocyte chamber 32 may be designed to be small, e.g., 15 micro-liters, thereby reducing waste of the perfusion solution.

Figure 7:
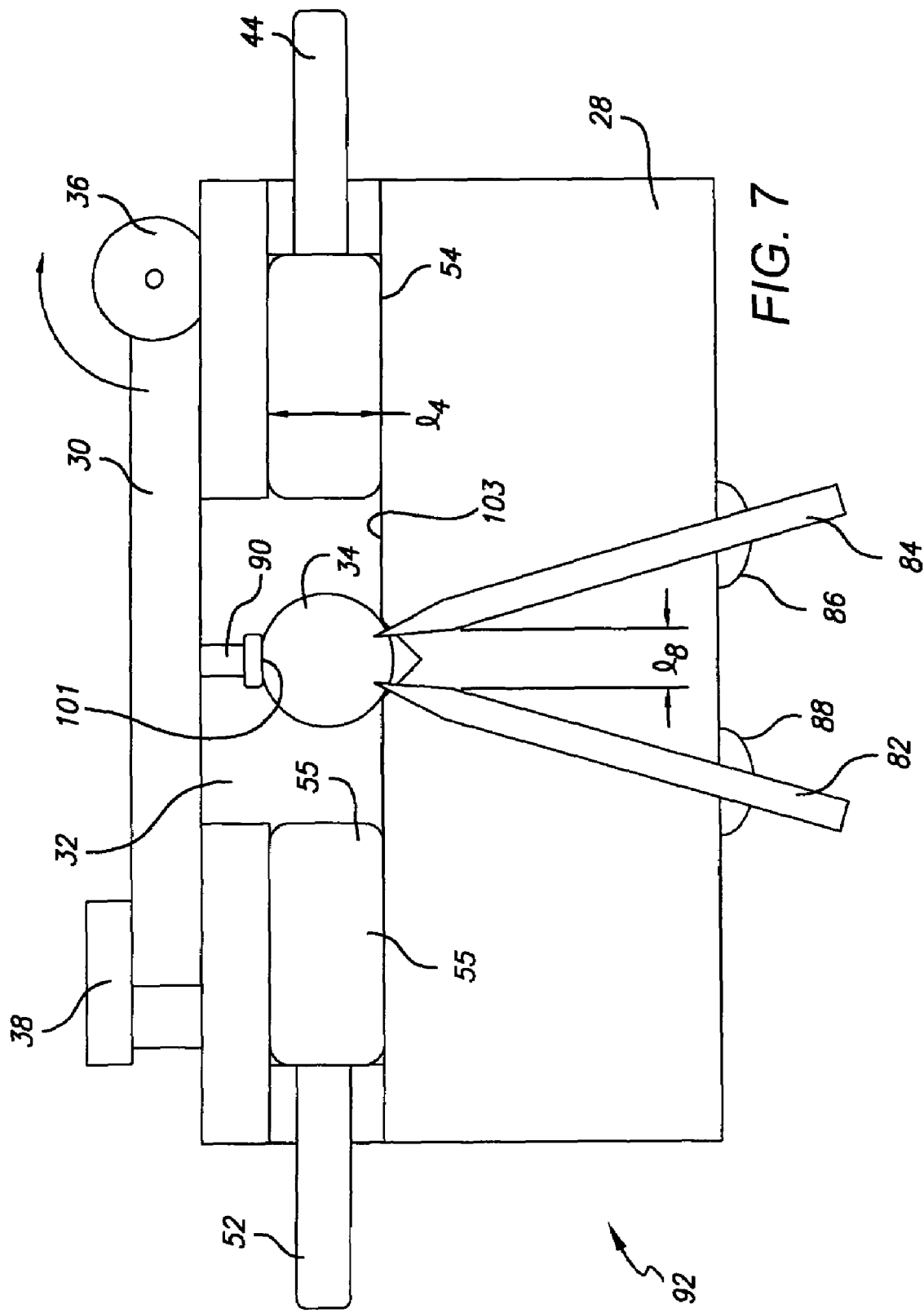
FIG. 7 shows a side view of an example of an oocyte recording chamber.

Referring to FIG. 7, a side view of another example a recording chamber 92 is shown. Recording chamber 92 includes a base 28 and a cover 30 that defines an oocyte chamber 32 that accommodates an oocyte 34. Cover 30 is rotatably coupled to base 28 through a hinge 36. A cover lock 38 secures cover 30 at a closed position to prevent movement of the cover during oocyte electrophysiological measurement. Similar to recording chamber 12, recording chamber 92 includes ground electrode connectors 44 and 52 (e.g., made of gold-plated brass), a gold-plated brass pellet 54, and a Ag—AgCl pellet 55.

A voltage electrode 82 and a current electrode 84 are embedded in base 28. The electrodes 82 and 84 are spaced slightly apart and at an angle relative to each other. Electrodes 82 and 84 are positioned so that the axes of the electrodes point toward the vicinity of the center of oocyte 34. Electrode 82 is secured by reinforcement material 88, and electrode 84 is secured by reinforcement material 86. A stopper 90 is connected to cover 30 and having a shape and size such that when cover 30 is closed, stopper 90 will slightly urge oocyte 34 towards the tips of electrodes 82 and 84 so that the tips may penetrate the membrane of the oocyte when the cover is fully closed.

In one example of recording chamber 92, the vertical distance $l_4$ between a surface 101 of stopper 90 facing oocyte 34 and a bottom surface 103 of oocyte chamber 32 is about 0.8 mm. The horizontal distance $l_8$ between the tips of electrodes 82 an 84 is about 0.5 mm.

Figure 8:
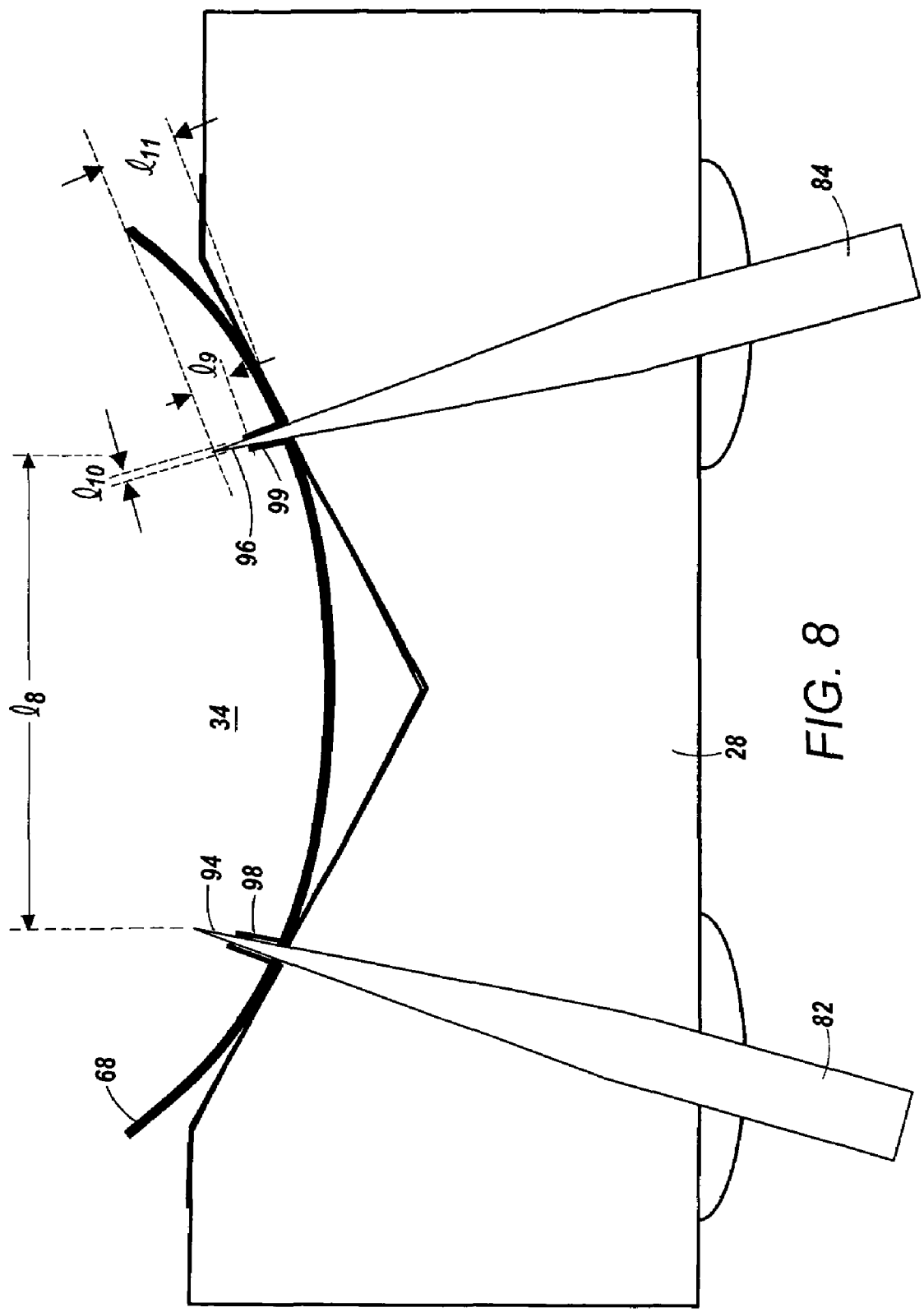
FIG. 8 shows a detailed view of the base and electrodes of the recording chamber of FIG. 7.

Referring to FIG. 8, electrodes 82 and 84 may be made of silver or platinum. In one example, electrode 84 is coated with silver/silver-chloride, while electrode 82 is not coated with silver/silver-chloride. Electrode 82 is coated with a polyamide layer 98 for the portion of the electrode extending into oocyte chamber 32, except for a small portion at a tip 94 that penetrates membrane 68 when cover 30 is closed. Electrode 84 is coated with a polyamide layer 99 for the portion of the electrode extending into the oocyte chamber 32, except for a small portion at the a 96 that penetrates membrane 68 when the cover 30 is closed. Polyamide layers 98 and 99 isolate tips 94 and 96, respectively, from the solution in the oocyte chamber 32.

In one example, the length $l_9$ of the portion of tip 96 not covered by polyamide layer 99 is about 70 microns. The diameter $l_8$ of the widest cross section of the portion of tip 96 not covered by polyamide layer 99 is about 25 microns. The length $l_9$ of tip 96 that penetrates into oocyte 34 is about 200 microns. Tip 94 may have similar dimensions. The thickness of polyamide layers 98 and 99 can be 10 to 20 microns.

Figure 9:
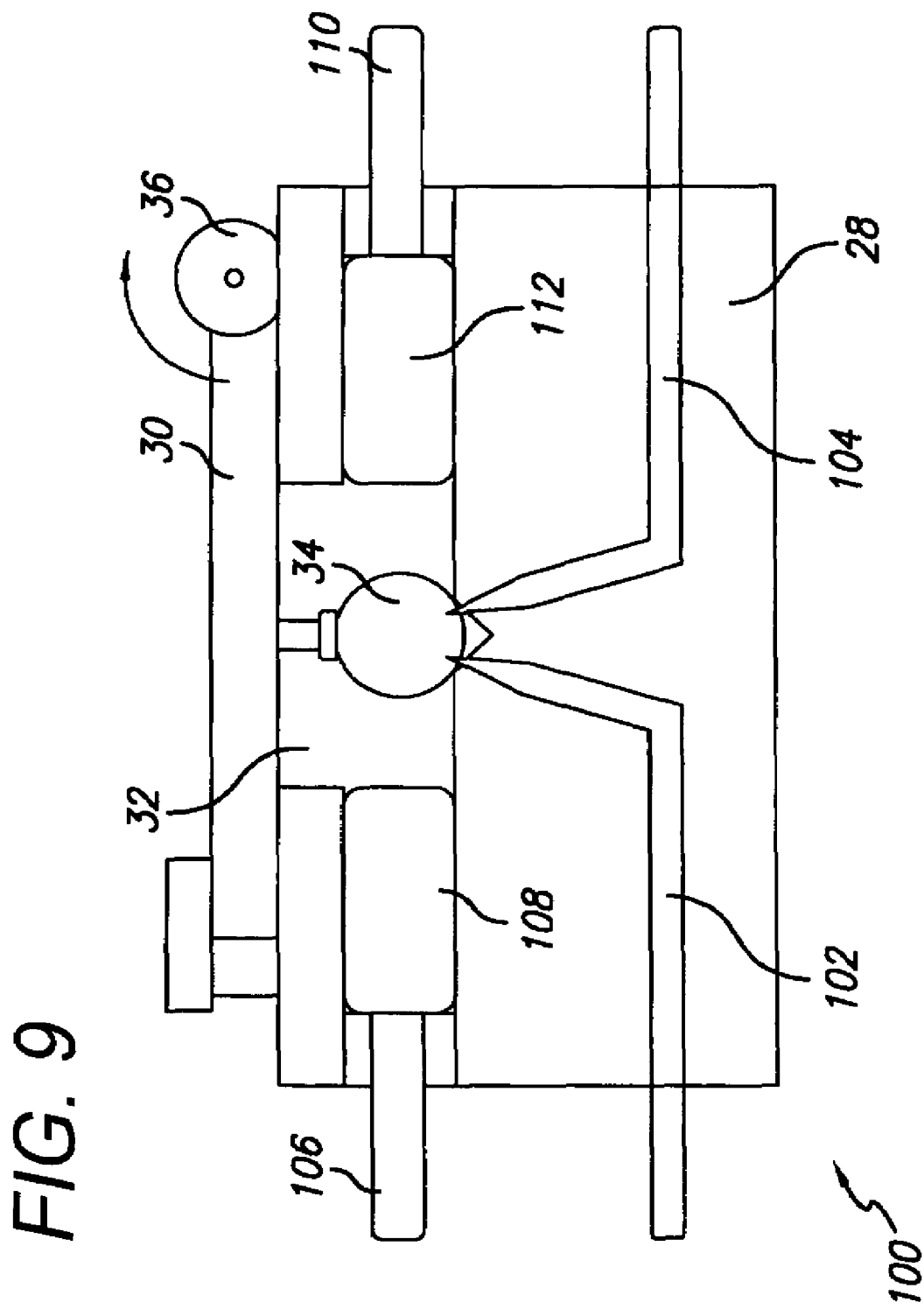
FIG. 9 shows a side view of an example of an oocyte recording chamber.

FIG. 9 is a side view of an example of a recording chamber 100. Recording chamber 100 includes a voltage electrode 102 and a current electrode 104 that are embedded in the base 28. The tip portions of electrodes 102 and 104 protruding into oocyte chamber 32 have configurations similar to those of electrodes 94 and 96. The body portion of electrodes 102 and 104 are bent inside base 28 so as to exit the base horizontally. A ground electrode connector 106 provides a ground reference for electrode 102, and a ground electrode connector 110 provides a ground reference for electrode 104. Ground electrode connectors 106 and 110 are coupled to pellets 108 and 112, respectively, which are exposed to oocyte chamber 32. Pellet 108 is similar to pellet 55 (FIG. 7), and pellet 112 is similar to pellet 54.

Figure 10:
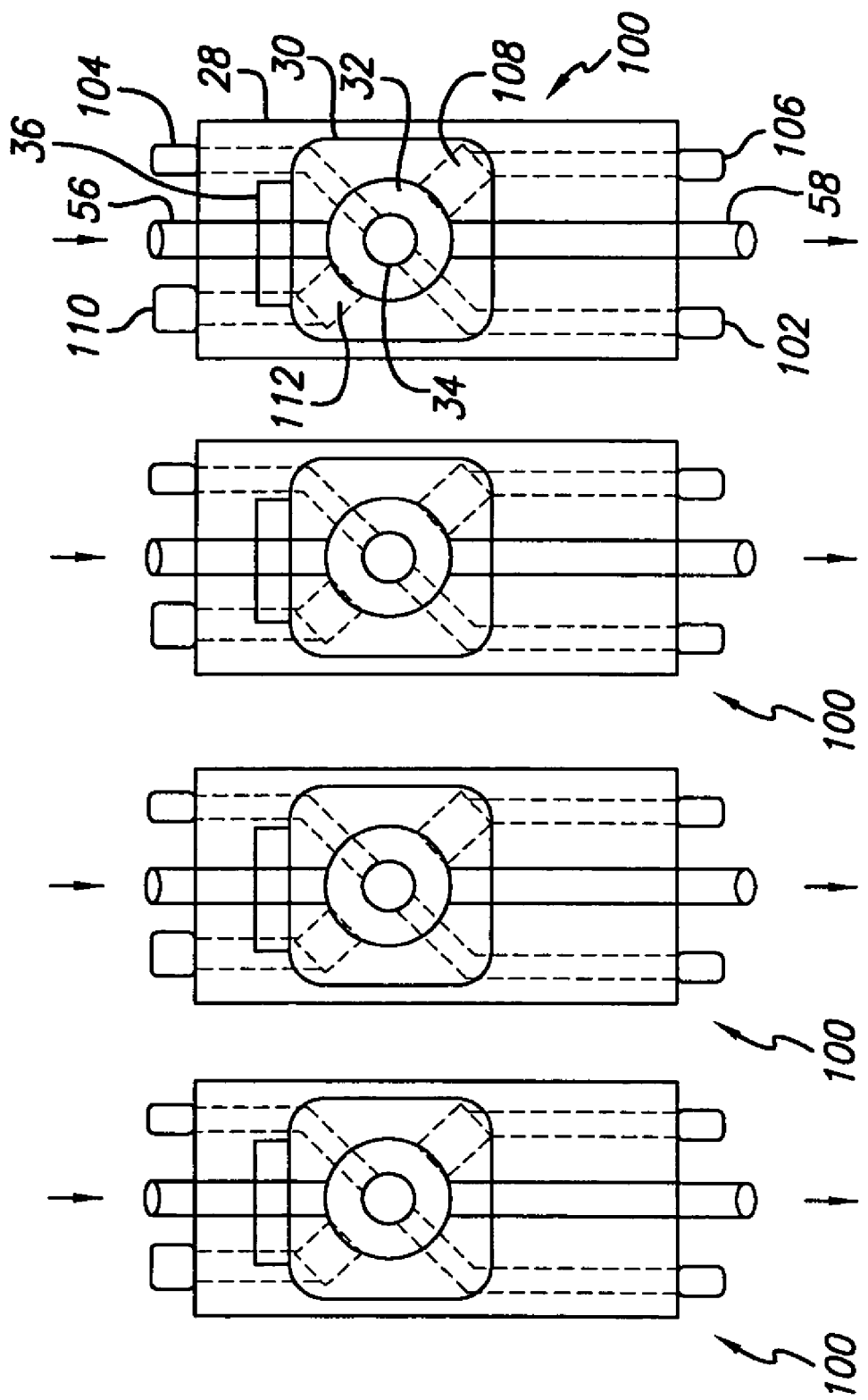
FIG. 10 shows a top view of recording chambers of FIG. 9 placed side by side.

FIG. 10 is a top view of recording chamber 100. Voltage electrode 102 and current electrode 104, and ground electrodes 106 and 110 all exit the base horizontally, but spaced apart so as to reduce clutter of electric wiring. By positioning the electrodes to exit the base along a direction parallel to the direction of the flow of the solution, a number of recording chambers 100 may be placed side by side, so that several measurements may be conducted at the same time using a small desk space.

FIGS. 13 and 14 show a top view and a side view, respectively, of an example of a recording chamber 130 that uses glass electrodes. Recording chamber 130 includes a base 132, center cover 134, and side covers 146 and 147. Base 132 and center cover 134 in combination defines an oocyte chamber 136 to accommodate an oocyte 34. The bottom surface of oocyte chamber 136 has an indent 160 that receives oocyte 34 and prevents oocyte 34 from moving before the electrodes are inserted into the oocyte. Oocyte chamber 136 is connected to an inlet 138, which may be connected to reservoirs (e.g., 18 in FIG. 2) containing perfusion solutions. An outlet 140 allows the perfusion solution to flow out of chamber 136 due to gravity. Inlet 138 is positioned lower than outlet 140 to prevent the solution from flowing out faster than it is replenished in oocyte chamber 136; this allows oocyte to be immersed in the solution when oocyte electrophysiological measurements are performed.

A voltage electrode 142 and a current electrode 144 are inserted into oocyte chamber 136 horizontally. Voltage electrode 142 includes a glass micropipette 143 filled with a 3M KCl electrolyte solution. Micropipette 143 has an outer diameter of about 1.5 mm, and has an opening of about 1 micron at a tip that penetrates into oocyte 34 during electrophysiological measurements. One end 166 of micropipette 143 is immersed in a 3M KCl solution contained in a container 148. An electrode connector 150 connects the KCl solution to a reference voltage. Current electrode 144 has a configuration similar to voltage electrode 142, and includes a glass micropipette filled with a 3M KCl solution. An electrode connector 151 connects current electrode 144 to a current measurement device (not shown).

Ground electrodes 152 and 154 are inserted horizontally into oocyte chamber 136. Ground electrode 152 is a silver/silver-chloride (i.e., Ag—AgCl) pellet having an outer diameter of about 2 mm. Ground electrode 154 is a gold-plated brass pellet, also having an outer diameter of about 2 mm. Ground electrodes 152 and 154 are connected to ground electrode connectors 156 and 158, respectively. When electrophysiological analysis of oocyte 34 is performed, the voltage between electrode connectors 150 and 156 is set to a predetermined value, and the current flowing through electrode connectors 158 and 151 is measured.

Figure 15:
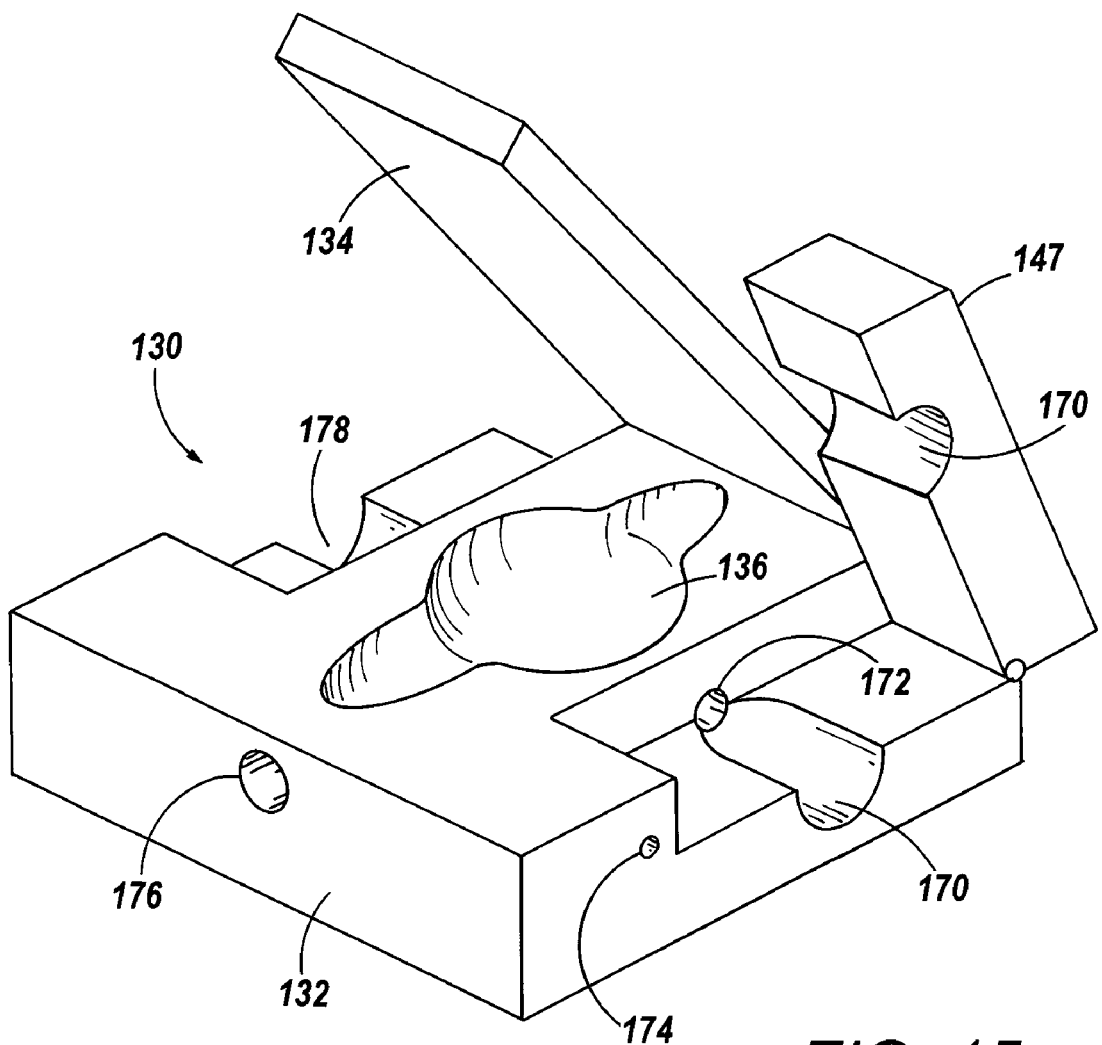
FIG. 15 shows a perspective view of a portion of the recording chamber in FIGS. 13 and 14.

FIG. 15 shows a perspective view of base 132, center cover 134, and side cover 147 (side cover 146 are omitted for clarity of illustration). Side cover 146 and base 132 define indents 170 that receive micropipette 143. Base 132 defines a passage 172 that connects oocyte chamber 136 and the space defined by indents 170. Side cover 146 and base 132 define indents 172 that receive micropipette 143. Base 132 defines a passage 174 that allows insertion of ground electrode connector 156. Base 132 also defines a passage 176 for inserting outlet 140, and another passage (not shown) for inserting inlet 138.

To set up recording chamber 130, center cover 134 and side covers 146, 147 are opened. Oocyte 34 is placed in the indent at the bottom surface of oocyte chamber 136. Voltage electrode 142 is positioned so that micropipette 143 is placed on the indent 170 on base 132 and inserted through passage 172 so that the tip of micropipette 143 contacts oocyte 34. Side cover 146 is then closed and acts like a clamp to hold micropipette 143 in place. Current electrode 144 is similarly positioned.

Returning to FIG. 13, recording chamber 130 includes gear mechanisms 162 and 163 that are coupled to knobs 164 and 165, respectively. Adjustment of the position of voltage electrode 142 is achieved by turning knob 164, which causes gear mechanism 162 to rotate and advances (or retracts) micropipette 143 towards (or away from) oocyte 34. Current electrode 144 can be adjusted in a similar way.

The following is an example of the dimensions of recording chamber 130. Base 132 has a width $l_{12}$ of about 15 mm, a length $l_{13}$ of about 25 mm, and a height $l_{14}$ of about 7.5 mm. Oocyte chamber 136 has a shape designed to have a small size but still allow sufficient contact between the perfusion solution and oocyte 34, and between the perfusion solution and ground electrodes 152 and 154.

An advantage of recording chamber 130 is that, after oocyte chamber 136 is filled with the perfusion solution, oocyte chamber 136 remains filled as long as the perfusion solution continues to be supplied to inlet 138. This eliminates solution level fluctuation problems associated with iterative filling and flushing of test and/or wash solutions into a chamber so that oocyte 34 may remain effective longer, and the oocyte response signals may be measured more accurately. Another advantage of recording chamber 130 is that, during positioning of electrode 142, micropipette 143 is clamped by base 132 and side cover 146 so that the micropipette 143 can only move along an axis 180 towards or away from oocyte 34. Likewise, the micropipette of electrode 144 can only move along an axis 182 towards or away from oocyte 34. This allows fast and simple adjustment of electrodes 142 and 144.

Candidate compounds or molecules for use in the processes described herein can be obtained from commercial sources or synthesized using methods and techniques known in the art. The compounds or molecules may be obtained individually or as part of a collection of library Although some implementations have been described, other embodiments are also within the scope of the following claims.

For example, the electrodes may be made of materials such as silver alloys or gold alloys, and the coating material (e.g., polyamide) may be substituted with other non-conductive and inert materials such as Teflon. The ground electrode pellets and ground electrode connectors can be made of materials other than those described above. The voltage and current electrodes may be coated with chemical layers that are stable in a physiological saline and can create reduced and stable junction potentials in the physiological saline. The base, cover, and stopper may be made of polypropylene. The voltage and current electrodes may both be embedded in the cover, with a stopper near the tip of each electrode. The shape of base 132, covers 134, 146, and 147 can vary, as can the dimensions of the apparatus, without substantially affecting the performance of the apparatus or method of use. Accordingly, other embodiments are within the scope of the following claims.

What is claimed is:

1. An apparatus, comprising: a base; a cover attached to the base; a stopper connected to the cover; a first electrode having a tip; a second electrode having a tip; a third electrode; and a fourth electrode; wherein:

(a) the cover is configured to be moveable between an open position to allow an oocyte to be placed in a chamber defined by the cover and the base and a closed position to form a seal between the cover and the base, the chamber having a size sufficient to accommodate an oocyte having a membrane, (b) the first electrode protrudes from the base and extends into the chamber and second electrode protrudes from the base or from the cover, and extends into the chamber, so that the tips of the first and second electrodes penetrate the membrane of the oocyte when the cover is in the closed position, (c) the third and fourth electrodes are both embedded in the base with portions of the electrodes exposed to the chamber, and (d) the stopper is configured to slightly press the oocyte towards the base, securing the oocyte position in the chamber when the cover is in the closed position.

2. The apparatus of claim 1 in which the stopper comprises a non-conducting material.

3. The apparatus of claim 2 in which the stopper comprises plastic or epoxy-glass.

4. The apparatus of claim 2 in which the second electrode protrudes from the cover and extends into the chamber.

5. The apparatus of claim 4, further comprising an isolation layer deposited on a portion of the second electrode exposed to the chamber except for a portion near a tip of the second electrode.

6. The apparatus of claim 5 in which the portion near the tip that is not covered by the isolation layer has a length between 50 to 100 microns.

7. The apparatus of claim 5 in which the portion of the second electrode exposed to the chamber has a length between 150 to 300 microns.

8. The apparatus of claim 5 in which the isolation layer comprises non-conducting polyamide.

9. The apparatus of claim 8, further comprising a stopper attached to the second electrode at a position between the cover and a tip of the second electrode, the stopper configured to slightly urge the oocyte towards the base when the cover is in the closed position.

10. An apparatus comprising: a stopper, a base; a cover attached to the base; a first electrode having a tip; a second electrode having a tip; a third electrode; and a fourth electrode; wherein (a) the cover is configured to be moveable between an open position to allow an oocyte to be placed in a chamber defined by the cover and the base and a closed position to form a seal between the cover and the base, the chamber having a size sufficient to accommodate an oocyte having a membrane, (b) the first and second electrodes are positioned so that the tips of the electrodes penetrate the membrane of the oocyte when the cover is in the closed position, and the third and fourth electrodes each have portions that are exposed to the chamber, (c) a portion of the base defines an indentation to receive the oocyte and to reduce movement of the oocyte in the chamber, and (d) the stopper is attached to a side of the cover facing the chamber, the stopper configured to slightly urge the oocyte towards the indentation when the cover is in the closed position.

11. A method of measuring the biological effect of a candidate molecule, comprising: providing a recording module having a base and a cover attached to the base, the cover is configured to be moveable between an open position and a closed position, the cover and the base defining a chamber having a size sufficient to accommodate a cell; providing a biosensor coupled to the base and facing the chamber; introducing the cell into the recording module; moving the cover to the closed position so that a water-tight seal is formed between the cover and the base, wherein moving the cover to the closed position simultaneously moves the cell towards the biosensor so that the biosensor penetrates a membrane of the cell; perfusing the chamber with perfusion solutions; and detecting a response of the cell to the solutions.

* * * * *